United States Patent [19]
Pettit et al.

[11] Patent Number: 5,529,989
[45] Date of Patent: Jun. 25, 1996

[54] PANCRATISTATIN PRODRUG

[75] Inventors: George R. Pettit, Paradise Valley, Ariz.; Sally Freeman, Birmingham, England

[73] Assignee: Arizona Board of Regents acting on behalf of Arizona State University, Tempe, Ariz.

[21] Appl. No.: 370,379

[22] Filed: Jan. 9, 1995

[51] Int. Cl.[6] ............... C07F 9/576; A61K 31/675
[52] U.S. Cl. .................................. 514/81; 546/23
[58] Field of Search ................... 514/81; 546/23

[56]     References Cited

U.S. PATENT DOCUMENTS 4,985,436  1/1991  Pettit ........................................ 514/287

OTHER PUBLICATIONS

Medicinal Chemistry, The Role of Organic Chemistry in Drug Research, 2nd Edition, 1993, Chapter 4, A. J. Collis, pp. 72–73.

*Primary Examiner*—Cecilia Tsang
*Attorney, Agent, or Firm*—Richard R. Mybeck; Walter R. Mybeck, II

[57]     ABSTRACT

Pancratistatin has been selected for pre-clinical development but is sparingly soluble in water. A disodium phosphate derivative has been synthesized which is water soluble and is bioequivalent thereof. The critical step in the synthesis of the phenolic phosphate was phosphorylation of 1,2,3,4-tetraacetoxy-pancratistatin with dibenzyloxy(N,N-diisopropylamido)phosphine. This pancratistatin prodrug has the structure set forth below:

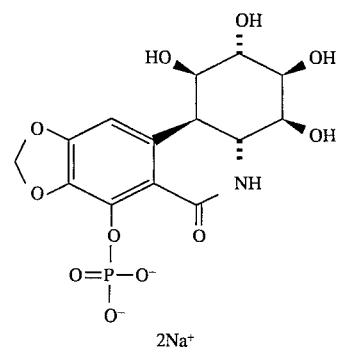

13 Claims, No Drawings

PANCRATISTATIN PRODRUG

This research was funded in part through Outstanding Investigator Grant CA 44344-01A1-04-06, and Grants CA-16049-05-12, awarded by the National Cancer Institute, DHHS. The United States Government may have certain rights to this invention.

INTRODUCTION

The present invention relates generally to the field of compositions useful in chemotherapy treatment for inhibiting leukemias, carcinomas and sarcomas and more particularly to water soluble salts of pancratistatin such as a disodium phosphate and a method of synthesis thereof.

BACKGROUND OF THE INVENTION

The isolation of pancratistatin was disclosed in U.S. Letters Pat. No. 4,985,436 issued Jan. 15, 1991. The general background therefrom relating to pancratistatin is incorporated herein, by this reference hereto, as if fully set forth.

As was noted in the above patent, pancratistatin is at best sparingly soluble in water. This substantially limits the availability of this drug in a form that could be administered in an aqueous solution. This has become significant since pancratistatin has been selected by the National Cancer Institute for pre-clinical development. Accordingly, the synthesis of a pancratistatin prodrug is important.

Therefore, the prime objective of the subject invention is to disclose the discovery of a disodium phosphate prodrug salt of pancratistatin which is a bioequivalent thereof.

BRIEF SUMMARY OF THE INVENTION

In 1984 the isolation of pancratistatin (1) from *Hymenocallis littoralis* (formerly *Pancratium littorale*) and the X-ray crystal structure determination of the 7-methoxy derivative was reported. The promising antineoplastic activity of pancratistatin (1) has led to its pre-clinical development and selection as an important synthetic target for a growing number of research groups. Pancratistatin is particularly attractive for clinical development due to its potent activity against experimental melanoma and ovary carcinoma. A related area of promise involves its activity against a range of RNA viruses. Unfortunately, pancratistatin exhibits very low water solubility (53 µg/ml) and this property has complicated its formulation for intravenous administration. While the solubility of this isocarbostyril can be increased in organic solvents such as dimethylformamide, dimethylsulfoxide and the lower boiling aliphatic alcohols, their use as formulation components is not desirable.

Complexation of pancratistatin (1) with a range of functionalized β-cyclodextrins and a series of other approaches did not significantly improve solubility. Therefore, it was decided to derivatize the drug with a bio-labile group chosen to improve water solubility. Because other phosphate prodrugs have recently been evaluated as anticancer compounds including prodrugs of Taxol and Combretastatin A-4 with the aim of improving their aqueous solubility this method was employed to circumvent the poor aqueous solubility of pancratistatin (1). The synthesis and biological evaluation of disodium phosphate derivative (5) that provides greatly increased water solubility (>230 mg/ml) is described herein. The phosphate prodrug of pancratistatin displays the same cancer cell growth inhibition as pancratistatin (1). Presumably, human non-specific phosphatases would release pancratistatin (1) following administration.

DESCRIPTION OF THE PREFERRED EMBODIMENT

STATISTICAL DEFINITIONS

The following measures are used to express drug activity by giving the drug dose which reduces cell growth to a specified percentage of growth:

$ED_{50}$ (P388) and $GI_{50}$ (HTCL) are the drug doses needed to reduce the percent growth to 50%. There is no mathematical difference between $ED_{50}$ and $GI_{50}$, which are both calculated using the same formula. The only difference is historical usage.

Total Growth Inhibition ("TGI"), is the drug dose needed to yield zero percent growth, i.e., just as many cells at the end of the experiment as were present in the beginning. Whether just as many cells were killed as were produced (steady state), or no growth occurred (total inhibition), cannot be distinguished.

Lethal Concentration 50% ("$LC_{50}$"), is the drug concentration which reduces growth to −50%, i.e., removes half of the cells originally present at the beginning of the experiment.

Each drug is tested at five (5) doses: 100—10—1—0.1—0.01 µg/ml. Percent Growths are calculated for each dose. The two (or three) doses with growth values above, below, (or near to) 50% growth are used to calculate the $ED_{50}/GI_{50}$ using a linear regression formula. The log of the dose is used during the regression computation. If no dose yields a growth value under 50%, the results are expressed as: $ED_{50}$>(highest dose). If no dose yields growth higher than 50% growth, then $ED_{50}$<(lowest dose). Similar calculations are performed for the TGI at 0% growth, and at −50% growth for the $LC_{50}$.

PERCENT OF GROWTH

At the start of an experiment, cells from the in vitro cell cultures are inoculated into the appropriate tubes or microtiter plates. One set of control tubes/plates is immediately counted to determine the number of cells at the start of the experiment. This is the "baseline count" or "$T_{zero}$ reading". At the end of the experiment (48 hours later) a second set of control tubes/plates is analyzed to determine the "Control Growth" value. The growth (or death) of cells relative to the initial quantity of cells is used to define the "Percent of Growth".

| | EXAMPLE:<br>Baseline Count = 20<br>Control Count = 200<br>(10-fold Growth) |
|---|---|
| 100% Growth = Control Growth | 100% Growth = 200 |
| 50% Growth = $T_{zero} + \dfrac{Control - T_{zero}}{2}$ | 50% Growth = 110 |
| 0% Growth = $T_{zero}$ | 0% Growth = 20 |
| −50% Growth = $T_{zero}/2$ | −50% Growth = 10 |

The flow chart of the synthesis of the pancratistatin prodrug is as appears below where pancratistatin is identified by reference (1) and the new disodium phosphate derivative is identified by the reference (5).

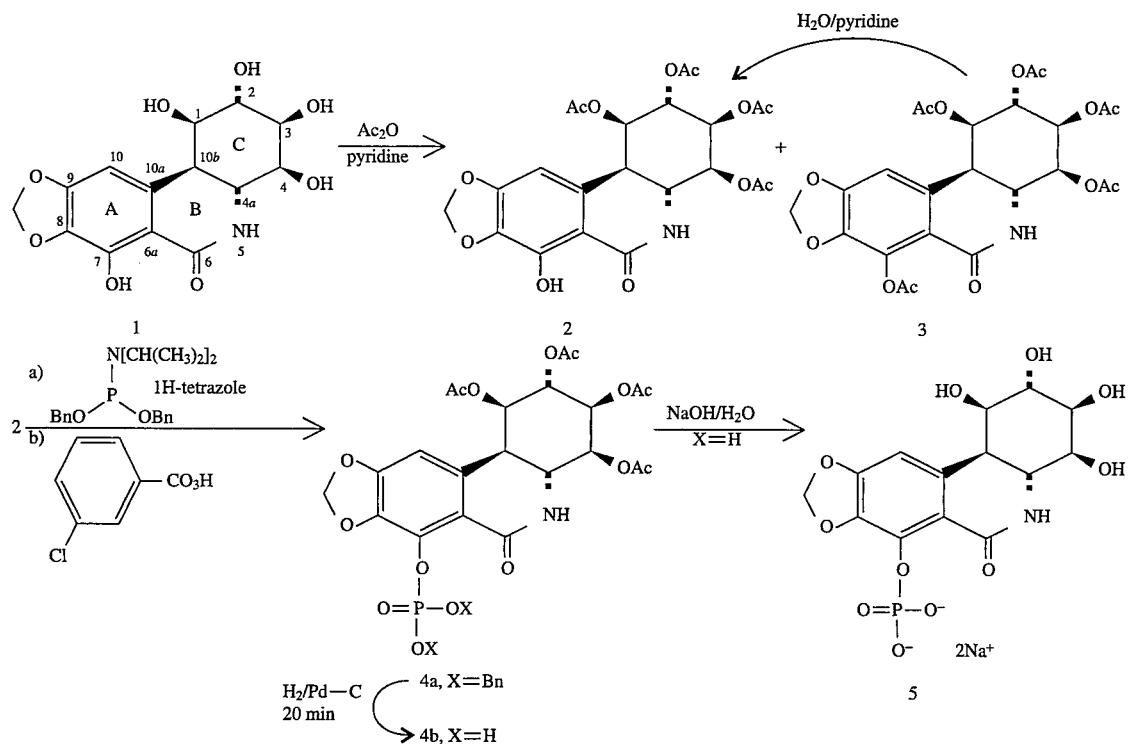

Selective phosphorylation of pancratistatin (1) is complicated by the A-ring phenolic hydroxyl group and the presence of four secondary alcohol groups in the C-ring. Investigations involving reactions with 2-cyanoethyl phosphate using dicyclohexylcarbodiimide coupling (G. M. Tener, 1961; "2 Cyanoethyl Phosphate and its use in the Synthesis of Phosphate Esters", 83 *J. Amer. Chem. Soc.* 159 (1961); indicated phosphorylation at two positions in the C-ring. A substantial effort was devoted to such approaches using pentavalent phosphorus derivatives.

Attention was next focused on selective protection of the pancratistatin C-ring hydroxyl groups. Derivatization by acetylation proved to be the most appropriate method. The phenolic hydroxy group of pancratistatin was soon found to be surprisingly unreactive, presumably due to its hydrogen-bonding to the lactam carbonyl. The 1,2,3,4-tetraacetoxy-pancratistatin (2) was obtained in good yield using acetic anhydride in pyridine. In prolonged reactions, 1,2,3,4,7-pentaacetoxy-pancratistatin (3) was also isolated. A mild procedure utilizing sodium bicarbonate to hydrolyse the phenolic ester proved unselective for conversion of pentaacetate (3) to tetraacetate (2). In contrast, the phenolic acetate was removed selectively by heating (at reflux for 25 minutes) in a solution of pyridine-water. The tetraacetate (2) structure was confirmed by results of; $^1H$, $^{13}C$, $^1H$—$^1H$ COSY and $^1H$—$^{13}C$ HMQC NMR spectroscopy.

Alkylamidophosphines are excellent reagents for the phosphorylation of alcohols and phenols in high yield See: J. W. Perich and R. B. Johns, "Di-tert-butyl N,N-Diethylphosphoramidite. A New Phosphitylating Agent for the Efficient Phosphorylation of Alcohols" *Synthesis* 142 (1988); K-L. Yu and B. Fraser-Reid, "A Novel Reagent for the Synthesis of Myo-Inositol Phosphates: N,N-Diisopropyl Dibenzyl Phosphoramidite" 29 *Tetrahedron Letters* 979 (1988); Y. Watanabe et al., "An Efficient Phosphorylation Method Using a New Phosphitylating Agent, 2-Diethylamino-1,3,2-Benzodioxaphosphopane", 31 *Tetrahedron Letters* 255 (1990); W. Thomson et al., "Synthesis bioactivation and Anti-HIV Activity of the Bis (4-acyloxybenzyl) and Mono(4-acyloxybenzyl) Esters of the 5'-Monophosphate of AZT", *Perkin Transactions* 1239 (1993); H-G. Chao et al., "N,N-Diisopropyl-bis[ 2-(trimethylsilyl) ethyl] phosphoramidite. An Attractive Phosphitylating Agent Compatible with the Fmoc/t-Butyl Strategy for the Synthesis of Phosphotyrosine Containing Peptides" 34 *Tetrahedron Letters* 337 (1993).

Dibenzyloxy(N,N-diisopropylamido)phosphine (K.-L. Yu and B. Fraser-Reid, supra at 29) was prepared in good yield from dichloro(N,N-diisopropylamido)phosphine (J. W. Perich and R. B. Johns, supra at 142) and benzyl alcohol. In the presence of the mild acid catalyst, 1H-tetrazole, this reagent phosphorylated the phenol group of pancratistatin tetraacetate (2). Without isolation, the resulting phosphinate was oxidized with m-chloroperbenzoic acid to give 7-(dibenzyloxyphosphoryl)-pancratistatin 1,2,3,4-tetraacetate (4a), which was purified by SILICA GEL column chromatography with a 91% yield. Quantitative cleavage of the benzyl protecting groups was achieved by rapid (20 min.) palladium catalyzed hydrogenolysis to give 7-phosphoryl-pancratistatin tetraacetate (4b). Selective hydrolysis of the four acetyl protecting groups was achieved with aqueous sodium hydroxide to give 7-phosphoryl-pancratistatin (5). The ionic byproducts were removed by anion-exchange chromatography using DEAE-SEPHADEX and gradient elution with an aqueous triethylammonium bicarbonate buffer (pH 7). The triethylammonium salt was converted (quantitatively) to the disodium phosphate (5) by passage through a DOWEX-50($Na^+$) cation exchange column. The structure of phosphate (5) was confirmed by analysis of the 2D-NMR ($^1H$—$^1H$ COSY and $^1H$—$^{13}C$ HMQC) and $^{31}P$-NMR spectral data.

Cancer cell growth inhibitory comparisons of pancratistatin (1) with its 7-phosphate derivative (5) gave very comparable results and suggested rapid loss of the phosphate ester. A direct comparison of the phosphate derivative (5) and the parent pancratistatin (1) against the U.S. National Cancer Institute's (NCI) panel of sixty human cancer cell lines showed comparable results for both compounds.

With the murine P388 lymphocytic leukemia cell line, phosphate (5) provided an $ED_{50}$ value of 0.032 µg/ml, which is essentially comparable to that found for pancratistatin (1). Consequently, the pancratistatin phosphate prodrug (5) is currently undergoing pre-clinical development.

General Methods

Pancratistatin (1) was isolated from *Hymenocallis littoralis* (Jacq.) Salisb. (Amaryllidaceae) grown in Tempe, Ariz. All solvents were distilled prior to use and dried when necessary. When available, reagent grade chemicals were employed and the 1H-tetrazole (99+% sublimed) was obtained from Sigma-Aldrich Chemical Company. Dibenzyloxy(N,N-diisopropylamido)phosphine was prepared as described by Thomson et al. supra at 1239 from benzyl alcohol and dichloro(N,N-diisopropylamido)phosphine.

SILICA GEL GHLF Uniplates were used for thin layer chromatography (TLC). The TLC plates were visualized under long-wave and short-wave UV and stained with iodine. For compounds containing phosphorus, the modified Jungnickel's reagent (perchloric acid-malachite green-sodium molybdate) developed by Vaskovsky and Latyshev "Rapid Chromatographic Technique for Preparative Separations with Moderate Resolution" 43 *J. Org. Chem.* 2923 (1978) was used. Flash column chromatography (Still et al., 1978) was performed with SILICA GEL 60 (230–400 mesh) from E. MERCK. The DOWEX 50X4-400 cation exchange resin was washed (prior to use) successively with aqueous 2 $\underline{N}$ hydrochloric acid, distilled water, aqueous $2\underline{N}$ sodium hydroxide and finally distilled water. DEAE SEPHADEX A-25 weak anion exchange resin (acetate form) was washed (before using) first with aqueous 1M triethylammonium bicarbonate (TEAB) buffer and then with 10 mM TEAB buffer.

Melting points were determined with an Electrothermal 9100 capillary apparatus and are uncorrected. Optical rotation values were recorded employing a PERKIN ELMER 241 polarimeter. The UV spectra were recorded using a PERKIN ELMER Lambda 3B UV/VIS Spectrophotometer interfaced to an IBM PC running PECSS data acquisition software. IR spectra were recorded on a Mattson Instruments 2020 Galaxy Series FT-IR. The $^1$H, $^{13}$C, $^1$H-$^1$H COSY, $^1$H-$_{13}$C HMQC and $^{31}$P-NMR spectroscopy experiments were conducted with VARIAN 300, 400 and 500-MHz instruments.

Method of Synthesis 1,2,3,4-Tetraacetoxy-Pancratistatin (2) (Method 1).

A solution of pancratistatin (1, 0.114 g, 0.350 mmol) in pyridine (10 ml)-acetic anhydride (2 ml) was stirred at room temperature under argon. After 5 hours, TLC (2% methanol in dichloromethane) showed that the majority of the pancratistatin had been converted to tetraacetate (2) (TLC $R_f$ 0.35). After concentration to a pale yellow oil, the tetraacetate (2) was isolated by column chromatography on SILICA GEL eluting with 1% methanol in dichloromethane. Fractions containing tetraacetate (2) were pooled to give a colorless solid (0.137 g, 79.5%). The tetraacetate (2) was recrystallized from methanol: m.p. 243.5–246° C.; U.V. $\lambda_{max}$ (CH$_2$Cl$_2$, nm, log ε) 236 (4.55), 281 (4.04) and 308 (3.57); $[\alpha]^{35}{}_D$+30.4° (c. 7.2 mg/ml, CH$_2$Cl$_2$); $^1$H-NMR δ$_H$ (499.8 MHz, CDCl$_3$, assignments made with the aid of a COSY spectrum) 12.37 (1H, s, 7-OH), 6.17 (1H, d, J$_{10/10b}$ 1 Hz, H-10), 6.08 (1H, s, 5-NH), 6.03 (2H, d, J$_{gem}$ 2.0 Hz, —OCH$_2$O—), 5.54 (1H, br t, J$_{1/2}$~J$_{1/10b}$~3.0 Hz, H-1), 5.45 (1H, br t, J$_{3/2}$~J$_{3/4}$~3.0 Hz, H-3), 5.21 (1H, t, J$_{2/1}$~J$_{2/3}$~3.0 Hz, H-2), 5.16 (1H, dd, J$_{4/4a}$ 11.0 Hz, J$_{4/3}$ 3.0 Hz, H-4), 4.28 (1H, dd, J$_{4a/10b}$ 13.0 Hz, J$_{4a/4}$ 11.0 Hz, H-4a), 3.42 (1H, ddd, J$_{10b/4a}$ 13.0 Hz, J$_{10b/1}$ 3.0 Hz, J$_{10b/10}$ 1.0 Hz, H-10b), 2.15 (3H, s, CH$_3$), 2.08 (6H, s, 2CH$_3$) and 2.03 (3H, s, CH$_3$); $^{13}$C-NMR δ$_c$ (125.7 MHz, CDCl$_3$, assignments deduced using APT and $^1$H—$^{13}$C HMQC correlation spectra) 169.9 (C=O), 169.8 (C=O), 169.5 (C=O), 169.0 (C=O), 168.2 (C=O), 153.3 (C-9), 146.8 (C-7), 133.5 (C-8), 131.7 (C-10a), 107.3 (C-6a), 102.4 (—OCH$_2$O—), 96.6 (C-10), 71.7 (C-4), 67.7 (C-2), 66.9 (C-3), 66.2 (C-1), 48.3 (C-4a), 39.3 (C-10b), 20.8 (CH$_3$), 20.7 (CH$_3$), 20.61 (CH$_3$) and 20.58 (CH$_3$); IR (KBr, cm$^{-1}$) 3341 (O—H stretch), 1753 (C=O ester) and 1674 (C=O lactam); m/z (low resolution FAB, 3-nitrobenzyl alcohol, glycerol, sodium carbonate) 516 (21%, [M+Na]$^+$) and 494 (100%, [M+H]$^+$); Found m/z (high resolution FAB) 516.1120. C$_{22}$H$_{23}$NO$_{12}$Na [M+Na]$^+$ requires 516.1118. Anal. calcd. for C$_{22}$H$_{23}$NO$_{12}$ C, 53.55; H, 4.70; N, 2.84. Found: C, 53.35; H, 4.83; N, 2.86%.

1,2,3,4-Tetraacetoxy-Pancratistatin (2) (Method 2).

In some of the preceding type acetylation reactions, 1,2,3,4,7-pentaacetoxy-pancratistatin (3) (G. R. Pettit et al., "Antineoplastic Agents," *J. Natural Prod.* 995 (1986)) was also formed upon prolonging the reaction time to 9 hours. Chromatographic separation as noted above gave tetraacetate (2) in 50% yield and pentaacetate (3) in 49% yield. (TLC $R_f$ 0.15 on SILICA GEL in 2% methanol in dichloromethane). Pentaacetate (3) was converted to tetraacetate (2) as follows. A solution of pentaacetate (3) (1.33 g, 2.48 mmol) in pyridine (30 ml) and water (20 ml) was heated at reflux for 25 minutes under argon. After concentration of the solvent, pyridine (25 ml) was added to azeotropically remove water, then toluene (25 ml) was added and removed (in vacuo) to displace pyridine. The residue was subjected to column chromatography as described in the above procedure to give tetraacetate (2) (0.98 g, 95% yield).

7-(Dibenzyloxyphosphoryl)-Pancratistatin 1,2,3,4 -Tetraacetate (4a).

To a vigorously stirred solution of 1,2,3,4-tetraacetoxy-pancratistatin (2), (1.0 g, 2.06 mmol, 1 equiv.) and dibenzyloxy(N,N-diisopropylamido)phosphine (2.13 g, 6.18 mmol, 3 equiv.) in dichloromethane (40 ml under argon at room temperature) was added 1H-tetrazole (0.58 g, 8.24 mmol, 4 equiv.). After 1 hour, the reaction mixture was cooled to –78° C. and a solution of m-chloroperbenzoic acid (2.25 g of a sample >57% pure, 3.6 equiv., dried over anhydrous magnesium sulfate) in dichloromethane (10 ml) was added by syringe over 1 minute. Cooling at –78° C was continued for 30 minutes and the turbid mixture was allowed to warm to room temperature over 30 minutes. The reaction mixture was successively washed with aqueous sodium bisulfite (10% w/v, 2×25 ml), aqueous sodium bicarbonate (saturated, 2×25 ml) and finally distilled water (25 ml). The organic layer was dried (anhydrous magnesium sulfate) and concentrated in vacuo to afford a yellow oil. The oil was purified by flash chromatography on SILICA GEL eluting with ethyl acetate-hexane (2:1) to give phosphate (4a) as a glassy colorless solid (1.41 g, 91% yield). The compound resisted crystallization from a range of solvents. A pure specimen was obtained from a SILICA GEL column eluting with 1% methanol in dichloromethane: m.p. 119°–121° C.; $[\alpha]^{33}{}_D$+69.1° (c. 8.9 mg/ml, CH$_2$Cl$_2$); U.V. $\lambda_{max}$ (CH$_2$Cl$_2$, nm, log ε) 261 (3.84) and 299 (3.72); $^1$H-NMR, $\delta_H$ (499.8 MHz, CDCl$_3$, assignments made with the aid of a COSY spectrum) 7.40–7.27 (10H, m, aromatic CH), 6.42 (1H, s, H-10), 6.41 (1H, s, 5-NH), 5.94 (1H, d, $J_{gem}$ 1.5 Hz, —OC H$_A$H$_B$O—), 5.90 (1H, d, $J_{gem}$ 1.0 Hz, —OCH$_A$H$_B$O—), 5.52 (1H, t, $J_{1/2}$~$J_{1/10b}$~2.0 Hz, H-1), 5.42 (1H, t, $J_{3/2}$~$J_{2/3}$~3.0 Hz, H-3), 5.38 (1H, dd, $J_{gem}$ 12.0 Hz, $J_{PH}$ 6.75 Hz, O—CH$_A$H$_B$Ph), 5.30 (1H, dd, $J_{gem}$ 12.0 Hz, $J_{PH}$ 6.75 Hz, O—CH$_A$H$_B$ Ph), 5.25 (1H, dd, $J_{gem}$ 12.0 Hz, $J_{PH}$ 7.0 Hz, O—C H$_C$H$_D$Ph), 5.22 (1H, dd, $J_{gem}$ 12.0 Hz, $J_{PH}$ 6.5 Hz, O—CH$_C$H$_D$Ph), 5.19 (1H, t, $J_{2/1}$~$J_{2/3}$~3.0 Hz, H-2), 5.13 (1H, dd, $J_{4/4a}$ 11.25 Hz, $J_{4/3}$ 3.75 Hz, H-4), 4.25 (1H, dd, $J_{4a/4}$ 10.75 Hz, $J_{4a/10b}$ 12.75 Hz, H-4a), 3.38 (1H, dd, $J_{10b/4a}$ 13.25 Hz, $J_{10b/1}$ 2.75 Hz, H-10b), 2.14 (3H, s, CH$_3$), 2.06 (3H, s, CH$_3$), 2.05 (3H, s, CH$_3$) and 2.03 (3H, s, CH$_3$); $^{13}$C-NMR $\delta_C$ (100.6 MHz, CDCl$_3$, assignments deduced using a $^1$H—$^{13}$C HMQC spectrum) 170.1 (C=O ester), 169.7 (C=O ester), 169.0 (C=O ester), 168.2 (C=O ester), 162.6 (C=O lactam), 152.4 (d, $J_{PC}$ 1.3 Hz, C-9), 139.3 (d, $J_{PC}$ 4.0 Hz, C-8), 136.0 (d, $J_{PC}$ 8.3 Hz, quaternary C of Ph), 135.9 (d, $J_{PC}$ 8.3 Hz, quaternary C of Ph), 134.2 (d, $J_{PC}$ 7.1 Hz, C-7), 133.0 (C-10a), 128.42 (2CH of Ph), 128.37 (2CH of Ph), 128.3 (2CH of Ph), 127.9 (2CH of Ph), 127.7 (2CH of Ph), 116.95 (d, $J_{PC}$ 3.4 Hz, C-6a), 102.7 (—OCH$_2$O—), 101.5 (C-10), 71.6 (C-4), 70.2 (d, $J_{PC}$ 5.8 Hz, OCH$_2$Ph), 70.0 (d, $J_{PC}$ 6.1 Hz, OCH$_2$Ph), 67.6 (C-2), 66.7 (C-3), 66.4 (C-1), 47.6 (C-4a), 40.3 (C-10b), 20.78 (CH$_3$), 20.75 (CH$_3$), 20.68 (CH$_3$) and 20.55 (CH$_3$); $^{31}$P-NMR $\delta_P$ (202.3 MHz, CDCl$_3$) −6.42 (s, $^1$H decoupled), (pentet $J_{PH}$ 6.9 Hz, $^1$H coupled); IR (film, cm$^{-1}$) 1753 (C=O ester), 1672 (C=O lactam) and 1292 (P=O stretch); m/z (low resolution FAB, 3-nitrobenzyl alcohol, glycerol, trifluoroacetic acid) 754.2 (100%, [M+H]$^+$), 694.2 (5%, [M+H−AcOH]$^+$), 646.1 (3%), 556.1 (8%) and 491.1 (5%); Found m/z (high resolution FAB) 754.1882, C$_{36}$H$_{37}$NO$_{15}$P ([M+H]$^+$) requires 754.1901. Anal. calcd. for C$_{36}$H$_{36}$NO$_{15}$NP C, 57.37; H, 4.81; N, 1.86%. Found: C, 57.47; H, 5.08; N, 1.72%.

Disodium 7-Phosphoryl-Pancratistatin (5).

To a stirred solution of 7-(dibenzyloxyphosphoryl)-pancratistatin 1,2,3,4-tetraacetate (4a) (1.41 g, 1.87 mmol) in absolute ethanol (140 ml) under an atmosphere of argon was added 10% palladium-on-carbon (0.5 g). The reaction mixture was purged with hydrogen and left for 20 minutes under a positive pressure (balloon) of hydrogen stirring vigorously. The solution was filtered through Celite and the filtrate was concentrated to afford phosphoric acid (4b) as a colorless solid: $^1$H-NMR, $\delta_H$ (300.1 MHz, D$_2$O, referenced to HOD at 4.77 ppm) 6.54 (1H, s, H- 10), 6.13 (1H, s, —OC H$_A$H$_B$O—), 6.09 (1H, s, —OCH$_A$H$_B$O—), 5.65 (1H, t, $J_{HH}$ 2.5 Hz, H-1,2 or 3), 5.52 (1H, t, $J_{HH}$ 3.3 Hz, H-1,2 or 3), 5.32 (1H, t, $J_{HH}$ 3.1 Hz, H-1,2 or 3), 5.28 (1H, dd, $J_{4/4a}$ 10.7 Hz, $J_{4/3}$ 3.5 Hz, H-4), 4.35 (1H, dd, $J_{4a/4}$ 12.8 Hz, $J_{4a/10b}$ 13.0 Hz, H- 4a), 3.68 (1H, dd, $J_{10b/4a}$ 13.0 Hz, $J_{10b/1}$ 2.3 Hz, H-10b), 2.20 (3H, S, CH$_3$), 2.15 (3H, S, CH$_3$), 2.13 (3H, S, CH$_3$) and 2.08 (3H, s, CH$_3$). The phosphoric acid (4b) was found to be unstable. Therefore, it was immediately neutralized by the addition of water (70 ml) containing sodium hydroxide (450 mg, 11.2 mmol, 6 equiv.). After 10 minutes, the solution was diluted to 1L with water and placed on a DEAE-SEPHADEX weak anion exchange column (50 ml, pre-equilibrated with 10 mM aqueous triethylammonium bicarbonate buffer [TEAB]). The column was eluted with a linear gradient of TEAB buffer (10–500 mM, 1L+1L). By TLC (2-propanol: ammonium hydroxide: water, 7-1-2) the fluorescent fractions containing phosphorus eluted at a concentration of 150–250 mM TEAB buffer. These were combined and concentrated (care was taken to ensure that the pH never dropped below 7 by the addition of small quantities of aqueous sodium hydroxide) and 2-propanol (5 ml) was added and removed by concentration to displace the TEAB buffer. This procedure was repeated twice with 5 ml aliquots of 2-propanol. A solution of the residue in water (25 ml) was applied to a DOWEX-50 cation exchange column (50 ml, Na$^+$ form). The column was eluted with water (150 ml) and the eluent was concentrated to give disodium 7-phosphorylpancratistatin (5) as a glass in a quantitative yield (0.89 g), [α]$^{35}$$_D$+107.35° (c. 10.2 mg/ml, H$_2$O); UV $\lambda_{max}$ (H$_2$O, nm, log ε) 212 (4.26), 227 (4.35), 270 (3.76) and 301 (3.58); IR (KBr, ) cm$^{-1}$) 3395 (br, O—H stretch), 3293 (br, O—H stretch), 1657 (C=O lactam) and 1111 (P=O stretch); $^1$H-NMR, $\delta_H$ (300.1 MHz, D$_2$O, referenced to 1,4-dioxane at 3.54 ppm, assignments made with the aid of a $^1$H—$^1$H COSY spectrum) 6.51 (1H, s, H-10), 5.89 (1H, d, $J_{gem}$ 1.2 Hz, O—CH$_A$H$_B$—O), 5.79 (1H, d, $J_{gem}$ 1.2 Hz, O—CH$_A$C H$_B$—O), 4.32 (1H, br. s, H-1), 4.04 (1H, t, $J_{2/1}$~$J_{2/3}$~3.1 Hz, H-2), 3.86 (1H, t, $J_{3/2}$~$J_{3/4}$ 2.7 Hz, H-3), 3.74 (1H, dd, $J_{4/4a}$ 10.4 Hz, $J_{4/3}$ 3.1 Hz, H-4), 3.67 (1H, ~t, $J_{4a/4}$~$J_{4a/10b}$~11.2 Hz, H-4a) and 2.94 (1H, dd, $J_{10b/4a}$ 12.1 Hz, $J_{10b/1}$ 1.9 Hz, H-10b); $^1$C-NMR, $\delta_C$ (125.7 MHz, D$_2$O, referenced to 1,4-dioxane at 67.3 ppm, assignments based on interpreting a $^1$H—$^{13}$C HMQC spectrum) 167.3 (C=O), 152.8 (C-9), 139.6 (C-8), 138.3 (d, $J_{PC}$ 6.1 Hz, C-7), 135.7 (C-10a), 118.4 (C-6a), 102.8 (—OCH$_2$O), 101.2 (C-10), 73.4 (C-3), 71.3 (C-2), 70.9 (C-4), 69.4 (C-1), 49.7 (C-4a) and 41.4 (C-10b); $^{31}$P-NMR $\delta_P$ (202.3 MHz, D$_2$O, $^1$H decoupled) 1.40 ppm; m/z (low resolution FAB, 3-nitrobenzyl alcohol, glycerol, trifluoroacetic acid) 472 (30%, [M + Na]$^+$), 450 (50%, [M+H]$^+$), 428 (25%, [M+2H−Na]$^+$), 348 (30%, [pancratistatin+Na]$^+$), 326 (75%, [pancratistatin+H]$^+$), 268 (75%), 246 (100%), 226 (50%) and 207 (85%); Found m/z (high resolution FAB) 450.0167, C$_{14}$H$_{15}$NO$_{11}$PNa$_2$ [M+H]$^+$ requires 450.0178. An analytically pure sample was prepared by precipitation of an aqueous solution with methanol, m.p. 197°–202° C. (dec). Anal. calcd. for C$_{14}$H$_{14}$NO$_{11}$PNa$_2$.3H$_2$O C, 33.41; H, 4.01; N, 2.78%. Found: C, 33.04; H, 3.81; N, 2.69%.

Pancratistatin (1) has been subjected to substantial in vivo testing. For example, the following data contained in U.S. Pat. No. 4,985,436, is repeated below for ready reference.

EXAMPLE 2 from U.S. Pat. No. 4,985,436

Unit dosage forms of pancratistatin prepared in accordance to selected compositions described in Example 1 were screened utilizing Protocol 1,200 described in *Cancer Chemotherapy Reports*, part 3, Vol. 3, No. 2, Sept. 1972, pp 9 et seq for lymphocytic leukemia P388. Pancratistatin provided a 38–106% life extension at 0.75–12.5 mg/kg host body weight against the murine P388 lymphocytic leukemia. Pancratistatin also markedly inhibited growth of the P388 in vitro cell line (ED$_{50}$, 0.001 μg/ml).

EXAMPLE 4 from U.S. Pat. No. 4,985,436

A unit dosage form of pancratistatin, prepared according to Example 1, was challenged with M5074 murine ovary sarcoma and obtained a 53% to 84% life extension at 0.38 to 3.0 mg active reagent/kg host body weight using the National Cancer Institute accepted protocol for life extension.

EXAMPLE 5 from U.S. Pat. No. 4,985,436

A unit dosage form of pancratistatin, prepared according to Example 1, was subjected to the National Cancer Institute accepted protocol for cure rate against its M5074 murine ovary sarcoma and obtained a 50% cure rate at 6 mg/kg host body weight.

Similarly, both compounds (1) and (5) have been subjected to standardized in vitro testing. Cancer cell growth inhibitory comparisons of pancratistatin (1) with its 7-phosphate derivative (5) gave very comparable results and suggested rapid loss of the phosphate ester. A direct comparison of phosphate (5) and the parent pancratistatin (1) against the U.S. National Cancer Institute's (NCI) panel of sixty human cancer cell lines showed comparable results for both compounds.

With the murine P388 lymphocytic leukemia cell line, phosphate (5) provided an $ED_{50}$ value of 0.032 μg/ml, which is essentially comparable to that found for pancratistatin (1). Consequently, the pancratistatin phosphate prodrug (5) is currently undergoing pre-clinical development.

Based upon the testing above, compound (5) is believed useful in treating neoplastic disease, for example, acute myelocytic leukemia, acute lymphocytic leukemia, malignant melanoma, adenocarcinoma of lung, neuroblastoma, small cell carcinoma of the lung, breast carcinoma, colon carcinoma, ovarian carcinoma, bladder carcinoma, and the like.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies either the compound designated herein as pancratistatin prodrug.

COMPOSITION "A"

Hard-Gelatin Capsules

One thousand two-piece hard gelatin capsules for oral use, each capsule containing 200 mg of an active ingredient are prepared from the following types and amounts of ingredients:

| | |
|---|---|
| Active ingredient, micronized | 200 g |
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 50, 250 and 500 mg amounts by substituting 50 g, 250 g and 500 g of an active ingredient for the 200 g used above.

COMPOSITION "B"

Soft Gelatin Capsules

One-piece soft gelatin capsules for oral use, each containing 200 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

COMPOSITION "C"

Tablets

One thousand tablets, each containing 200 mg of an active ingredient, are prepared from the following types and amounts of ingredients:

| | |
|---|---|
| Active ingredient, micronized | 200 g |
| Lactose | 300 g |
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 250 mg and 100 mg amounts by substituting 250 g and 100 g of an active ingredient for the 200 g used above.

COMPOSITION "D"

Oral Suspension

One liter of an aqueous suspension for oral use, containing in each teaspoonful (5 ml) dose, 50 mg of an active ingredient, is prepared from the following types and amounts of ingredients:

| | |
|---|---|
| Active ingredient, micronized | 10 g |
| Citric acid | 2 g |
| Benzoic acid | 1 g |
| Sucrose | 790 g |
| Tragacanth | 5 g |
| Lemon Oil | 2 g |
| Deionized water, q.s. | 1000 ml |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

COMPOSITION "E"

Parenteral Product

A sterile aqueous suspension for parenteral injection, containing 30 mg of an active ingredient in each milliliter for treating a neoplastic disease, is prepared from the following types and amounts of ingredients:

| | |
|---|---|
| Active ingredient, micronized | 30 g |
| POLYSORBATE 80 | 5 g |
| Methylparaben | 2.5 g |
| Propylparaben | 0.17 g |
| Water for injection, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 ml) three times a day.

COMPOSITION "F"

Suppository, Rectal and Vaginal

One thousand suppositories, each weighing 2.5 g and containing 200 mg of an active ingredient are prepared from the following types and amounts of ingredients:

| Active ingredient, micronized | 15 g |
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

COMPOSITION "G"

Intranasal Suspension

One liter of a sterile aqueous suspension for intranasal instillation, containing 20 mg of an active ingredient in each milliliter, is prepared from the following types and amounts of ingredients:

| Active ingredient, micronized | 15 g |
| POLYSORBATE 80 | 5 g |
| Methylparaben | 2.5 g |
| Propylparaben | 0.17 g |
| Deionized water, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

COMPOSITION "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

One hundred grams of an active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

COMPOSITION "J"

Insufflation

One hundred grams of an active ingredient in bulk form is finely divided by means of an air micronizer.

The foregoing composition is useful for treating a neoplastic disease, by the inhalation of 300 mg one to four times a day.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies the pancratistatin disodium phosphate derivative designated herein as compound (5).

From the foregoing, it becomes readily apparent that a new and useful antineoplastic factor and new and useful antineoplastic preparations have been herein described and illustrated which fulfill all of the aforestated objectives in a remarkably unexpected fashion. It is, of course, understood that such modifications, alterations and adaptions as will readily occur to the artisan confronted with this disclosure are intended within the spirit of the present invention which is limited only by the scope of the claims appended hereto.

Accordingly, what is claimed is:

1. A composition of matter having the structural formula set forth below:

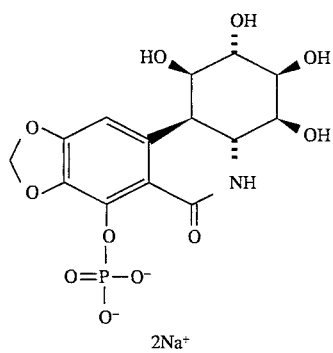

2. A composition of matter according to claim 1 disposed in water.

3. A composition of matter according to claim 1 which is substantially pure.

4. A pharmaceutical preparation for treating a mammalian host afflicted with a neoplastic disease selected from the group consisting of lymphocytic leukemia, ovarian cancer, breast cancer, small cell lung cancer, non-small cell lung cancer, renal cancer, CNS cancer, melanoma, and colon cancer, said preparation containing a pharmaceutically acceptable carrier and, as its essential active ingredient a compound having the structural formula set forth below:

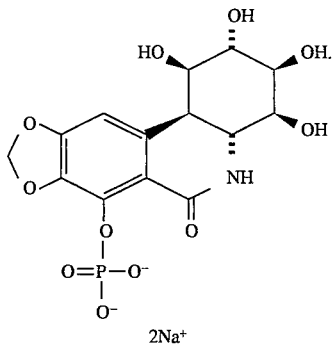

5. A pharmaceutical preparation according to claim 4 wherein said pharmaceutically acceptable carrier is water.

6. A pharmaceutical preparation according to claim 5 for treating lymphocytic leukemia.

7. A pharmaceutical preparation according to claim 5 for treating ovarian cancer.

8. A method of treating a mammalian host afflicted with a neoplastic disease selected from the group consisting of lymphocytic leukemia, breast cancer, small cell lung cancer, non-small cell lung cancer, ovarian cancer, renal cancer, CNS cancer, melanoma, and colon cancer, comprising administering to said host the active ingredient whose structure is set forth below in a pharmaceutically acceptable carrier at a concentration sufficient to provide from about 0.1 to about 10 mg/kg of host body weight daily.

9. A method according to claim 8 in which said pharmaceutically acceptable carrier is water.

10. A method according to claim 9 wherein said disease is ovarian cancer.

11. A method according to claim 10 wherein said dosage range is from about 5 to about 15 mg/kg host body weight daily.

12. A method according to claim 9 wherein said disease is lymphocytic leukemia.

13. A method according to claim 12 wherein said dosage is from about 0.75 to about 12.5 mg/kg host body weight daily.

* * * * *